United States Patent

Balzer et al.

[11] 3,970,647
[45] July 20, 1976

[54] BIS-(TRIAZINYLAMINO)STILBENE COMPOUNDS

[75] Inventors: Hans Balzer, Munchenstein; Fritz Fleck, Bottmingen; Hans-Rudolf Schmid, Riehen, all of Switzerland

[73] Assignee: Sandoz Ltd., Basel, Switzerland

[22] Filed: Feb. 11, 1974

[21] Appl. No.: 441,376

[30] Foreign Application Priority Data
Feb. 16, 1973  Switzerland.................. 2326/73

[52] U.S. Cl. .......................... 260/240 B; 427/158
[51] Int. Cl.² ..................................... C07D 251/04
[58] Field of Search ............... 260/240 B; 427/158

[56] References Cited
UNITED STATES PATENTS

| | | | |
|---|---|---|---|
| 3,018,287 | 1/1962 | Fleck................. | 260/240 B |
| 3,051,704 | 8/1962 | Gelm et al......... | 260/240 B |
| 3,479,349 | 11/1969 | Allison et al..... | 260/240 B |
| 3,503,953 | 3/1970 | Loffelman.......... | 260/240 B X |
| 3,546,218 | 12/1970 | Tscharner.......... | 260/240 B |
| 3,600,385 | 8/1971 | Loffelman et al. | 260/240 B |
| 3,663,538 | 5/1972 | Lebkucher et al. | 260/240 B |
| 3,676,339 | 7/1972 | Tscharner.......... | 260/240 B X |
| 3,757,010 | 9/1973 | Balzer et al...... | 260/240 B |

FOREIGN PATENTS OR APPLICATIONS

| | | | |
|---|---|---|---|
| 859,155 | 12/1970 | Canada............... | 260/240 B |
| 1,551,263 | 11/1968 | France................ | 260/240 B |
| 1,299,120 | 12/1972 | United Kingdom | |

Primary Examiner—Allen B. Curtis
Attorney, Agent, or Firm—Gerald D. Sharkin; Richard E. Vila; Joseph J. Borovian

[57] ABSTRACT

Disclosed are stilbene compounds of formula I,

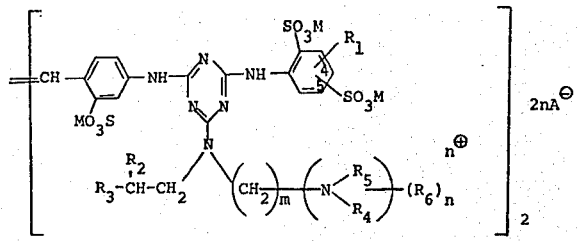

in which
  $R_1$ signifies hydrogen, halogen or $C_{1-6}$ alkyl,
  $R_2$ signifies hydrogen or methyl,
  $R_3$ signifies cyano or a radical $-CONR_7R_8$ in which either $R_7$ and $R_8$, independently, each signifies hydrogen, $C_{1-6}$alkyl or $C_{2-6}$hydroxyalkyl, or $R_7$ and $R_8$, together with the nitrogen atom, signify a pyrrolidine, piperidine or morpholine radical,
either $R_4$ and $R_5$, independently, each signifies
  $C_{1-6}$alkyl or $C_{2-6}$hydroxyalkyl, or $R_4$ and $R_5$, together with the nitrogen atom, form a radical (a)

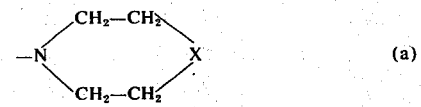

(a)

in which
  $-X-$ signifies $-CH_2-$, $-O-$, $-S-$, a direct bond, or $-NR_9-$, in which $R_9$ signifies $C_{1-6}$alkyl or $C_{2-6}$hydroxy-alkyl,
  $R_6$ signifies hydrogen or $C_{1-6}$alkyl, unsubstituted or substituted by hydroxy, cyano or aminocarbonyl,
  M signifies hydrogen or a non-chromophoric cation,
  $A^-$ signifies a non-chromophoric anion
  m signifies 2 or 3, and
  n signifies 0 or 1,
the $-SO_3M$ group, shown floating, being bound to the 4- or 5-position of the benzene ring and, when n signifies 1, $R_6$ being bound either to the nitrogen or, when $NR_4R_5$ signifies a thiomorpholino ring, to the nitrogen or to the sulphur thereof or, when $NR_4R_5$ signifies a piperazine ring, to one or other of the nitrogens thereof, their production and use as optical brighteners on cellulosics, particularly on cotton and paper.

26 Claims, No Drawings

BIS-(TRIAZINYLAMINO)STILBENE COMPOUNDS

The invention relates to stilbene compounds.

According to the invention, there are provided compounds of formula I,

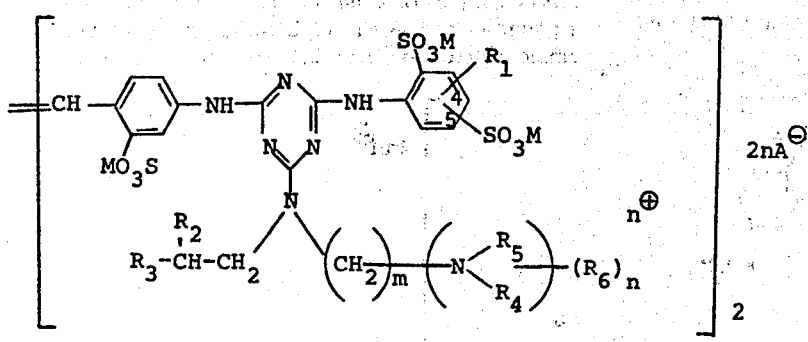

in which
- $R_1$ signifies hydrogen, halogen or $C_{1-6}$ alkyl,
- $R_2$ signifies hydrogen or methyl,
- $R_3$ signifies cyano or a radical $-CONR_7R_8$ in which either $R_7$ and $R_8$, independently, each signifies hydrogen, $C_{1-6}$alkyl or $C_{2-6}$hydroxyalkyl, or $R_7$ and $R_8$, together with the nitrogen atom, signify a pyrrolidine, piperidine or morpholine radical,
- either $R_4$ and $R_5$, independently, each signifies $C_{1-6}$alkyl or $C_{2-6}$hydroxyalkyl, or $R_4$ and $R_5$, together with the nitrogen atom, form a radical (a)

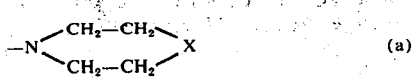

in which
- $-X-$ signifies $-CH_2-$, $-O-$, $-S-$, a direct bond, or $-NR_9-$, in which $R_9$ signifies $C_{1-6}$alkyl or $C_{2-6}$hydroxyalkyl,
- $R_6$ signifies hydrogen or $C_{1-6}$alkyl, unsubstituted or substituted by hydroxy, cyano or aminocarbonyl,
- M signifies hydrogen or a non-chromophoric cation,
- $A^-$ signifies a non-chromophoric anion
- $m$ signifies 2 or 3, and
- $n$ signifies 0 or 1, The $-SO_3M$ group, shown floating, being bound to the 4-or 5-position of the benzene ring and, when $n$ signifies 1, $R_6$ being bound either to the nitgoren or, when $NR_4R_5$ signifies a thiomorpholino ring, to the nitrogen or to the sulphur thereof or, when $NR_4R_5$ signifies a piperazine ring, to one or other of the nitrogens thereof.

In the compounds of formula I, any halogen as $R_1$ is fluorine, chlorine or bromine, chlorine being preferred. Any alkyl radical as $R_1$ is preferably of 1 to 4 carbon atoms, e.g. methyl, ethyl, n-propyl, iso-propyl, n-butyl, sec.butyl or tert.butyl, methyl and ethyl being preferred. The preferred significance of $R_1$ is hydrogen.

Where $R_4$ and $R_5$ signify alkyl, such is preferably of 2 to 6 carbon atoms. Preferred alkyl and hydroxyalkyl radicals as $R_4$ and $R_5$ are of 2, 3 or 4 carbon atoms. Where $R_4$ and $R_5$, together with the nitrogen atom, signify a radical (a), above, and X therein signifies $-NR_9-$, any alkyl radical as $R_9$ is preferably of 1 to 3 carbon atoms and any hydroxyalkyl radical as $R_9$ is preferably 2 to 3 carbon atoms. As specific examples of the group $-NR_4R_5$, may be given diethanolamino, di-(isopropanol)-amino, di-n-butylamino, di-n-propylamino, diethylamino, di-iso-propylamino, N-ethyl-N-butylamino, N-ethyl-N-propylamino, pyrrolidino, morpholino, piperidino, thiomorpholino, N-methylpiperazino, N-ethylpiperazino, N-(hydroxyethyl)-piperazino, N-(β-hydroxypropyl)-piperazino and N-iso-propylpiperazino radicals.

As examples of groups $-CO-NR_7R_8$, as $R_3$, may be given the methylamino-, ethylamino-, ethanolamino-, isopropanolamino-, propylamino-, butylamino-, dimethylamino-, diethylamino-, di-ethanolamino-, di-(isopropanol)-amino-, N-methyl-N-ethylamino-, N-methyl-N-propylamino-, N-methyl-N-butylamino-, pyrrolidino-, piperidino-, and morpholino-carbonyl groups, the preferred significance of $-CONR_7R_8$, however, being $-CONH_2$.

As examples of radical $R_6$, may be given methyl, ethyl, isopropyl, n-propyl, n-butyl, isobutyl, tert.butyl, n-amyl, isoamyl, n-hexyl, β-hydroxyethyl, β-hydroxypropyl, 2-hydroxybutyl-1 or -3, 2-cyanoethyl and 2-aminocarbonylethyl. The preferred significances of $R_6$ are methyl and ethyl, particularly the former.

Where M signifies a non-chromophoric cation, the exact nature thereof is not critical. As examples of suitable cations may be given those commonly employed in the optical brightener art, specific examples being the alkali-metal cations, e.g. of sodium, potassium and lithium, particularly the former, alkaline-earth metal cations, e.g. of magnesium, calcium, strontium, or barium; aluminum; ammonium; alkylammonium and substituted alkylammonium cations. The preferred ammonium cations can conveniently be represented by the formula $R_{12}R_{13}R_{14}R_{15}N^+$, where $R_{12}$, $R_{13}$, $R_{14}$ and $R_{15}$, independently, signify hydrogen or $C_{1-4}$alkyl, unsubstituted or substituted by one or two, preferably one, hydroxy group. As specific examples may be given the mono-, di- and triethanolammonium and the mono-, di- and tri-isopropanolammonium cations.

For the sake of simplicity, M, herein, has been represented as monovalent in the formulae. As will be appreciated, however, it may be multivalent, e.g. divalent when signifying an alkaline-earth metal cation and tri-valent when signifying an aluminum cation.

The significance of $A^-$, again, is not critical provided its significance is non-chromophoric. Conventional anions used in the optical brightener art may be employed, both organic or inorganic. As specific examples may be given the formate, chloracetate, propionate, oxalate, lactate, tartrate, benzoate, maleinate, chloride, bromide, iodide, perchlorate, methylsulphate, ethylsulphate, methylsulphonate, sulphate, bisulphate, benzenesulphonate, 4-methylbenzenesulphonate and, 4-chloro-benzenesulphonate ions. Hydrosoluble double salts such as of zinc chloride may also be mentioned. When, in the compounds of formula I, $R_6$ signifies hydrogen, i.e. in the case of acid adducts, $A^-$ preferably signifies an acetate, formate, chloride or bisulphate ion.

Preferred compounds of formula I are the compounds of formula I',

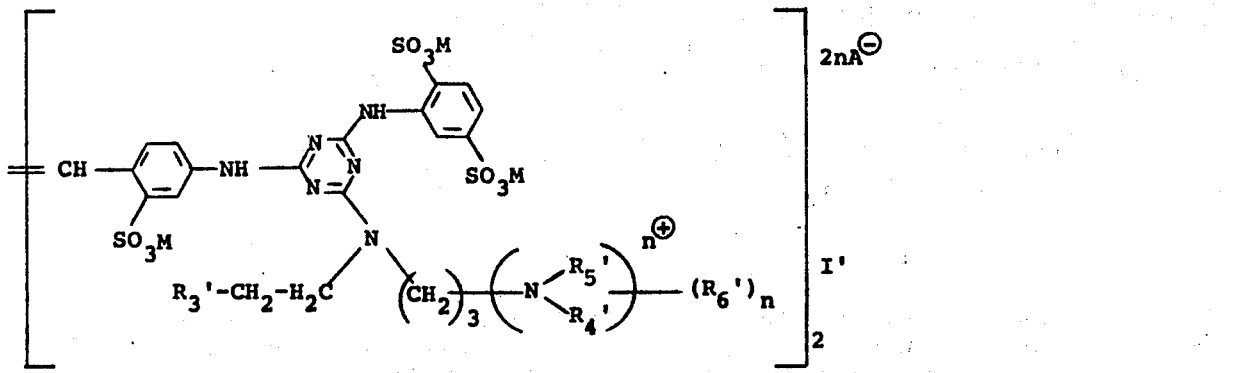

in which
$R_3'$ signifies —CN or —CONH$_2$,
either $R_4'$ and $R_5'$, independently, each signifies $C_{2-4}$alkyl,
or $R_4'$ and $R_5'$, together with the nitrogen atom, signify a pyrrolidine, piperidine, morpholine or N-methyl-piperazine ring,
$R_6'$ signifies hydrogen, methyl or ethyl, and
$A^-$, $n$ and M are as defined above.

The invention also provides a process for the production of the compounds of formula I stated above, characterised by reacting, in any desired order, a cyanuro halide with an amine of formula IV,

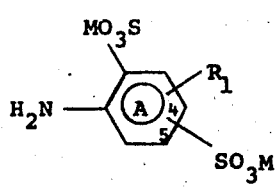

in which $R_1$ and M are as defined above, a compound of formula V,

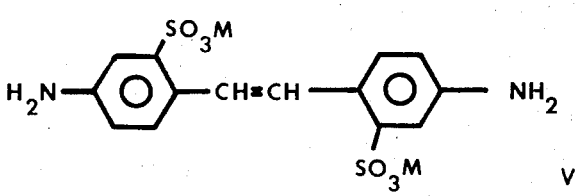

in which M is as defined above, an amine of formula VI,

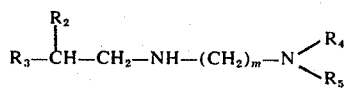

in which $R_2$, $R_3$, $R_4$, $R_5$ and $m$ are as defined above, and a quaternation or protonization agent corresponding to the radical $R_6$.

The mole ratio of cyanuro halide: compound IV: compound V: compound VI: the quaternation or protonization agent is preferably 2:2:1:2:$n$.

As examples of amines of formula IV may be given 1-amino-6-methylbenzene-2,4-disulphonic acid, 1-amino-5-methylbenzene-2,4-disulphonic acid, 1-amino-3-methylbenzene-2,4-disulphonic acid, 1-amino-4-chlorobenzene-2,5-disulphonic acid, 1-amino-5-chlorobenzene-2,4-disulphonic acid and preferably 1-aminobenzene-2,4-disulphonic acid, 1-aminobenzene-2,5-disulphonic acid and the M salts thereof.

The amines of formula VI, which may optionally be employed in salt form, are preferably produced by reacting amines of formula VII,

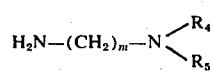

in which $R_4$, $R_5$ and $m$ are as defined above, optionally in salt form, with acrylic or methacrylic acid derivatives of formula VIII

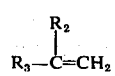

in which $R_2$ and $R_3$ are as defined above.

Specially preferred compounds of formula VIII are acrylonitrile, methacrylonitrile, acrylic amide or methacrylic acid amide. Further, the substituted acrylic amides and methacrylic amides (e.g. of the above-mentioned examples) may be employed.

Preferred compounds of formula VII are those wherein $m$ signifies 3, particularly 3-di-ethylamino-1-propylamine, 3-di-n-butylamino-1-propylamine, 3-di-(2-hydroxyethyl)-amino-1-propylamine, 3-morpholino-1-propylamine, 3-piperidino-1-propylamine, 3-pyrrolidino-1-propylamine, 3-(4'-methyl, -ethyl or -hydroxyethyl)-piperazino-1-propylamine and 3-thiomorpholino-1-propylamine.

Appropriate quaternation agents are, for example, esters of sulphuric acid, such as dimethylsulphate or diethylsulphate, or the esters of aromatic or aliphatic sulphonic acids, such as benzene-, 4-methylbenzene-, and 4-chlorobenzenesulphonic acid methyl, ethyl and n-butyl esters, and methane, ethane, 1-propane and 2-propane sulphonic acid methyl and -ethyl esters.

As alkylation agents may be used alkyl halides of 1 to 6 carbon atoms, optionally substituted by hydroxyl, cyano or aminocarbonyl groups, e.g. methyl chloride, methyl bromide, ethyl bromide, n-butyl bromide, 2-chloro- or 2-bromoethanol, chloracetonitrile and preferably chloro- or bromoacetic acid amide or β-chloropropionic acid amide.

As examples of quaternation agents, which are used in acid medium, i.e. when the quaternisable nitrogen atoms are protonized, may be given alkylene oxides, such as ethylene oxide or propylene oxide, as well as derivatives of acrylic acid, such as acrylonitrile and acrylic amide. The reaction of the compounds of formulae VII and VIII is preferably effected at temperatures of from 0° to 100°C.

The reaction of the cyanuro halides, e.g. cyanuro bromide and particularly cyanuro chloride, with the amino compounds is carried out in analogy with methods known per se. For example, the reaction is effected in aqueous medium, when the cyanuro halide is suspended only in water, or in aqueous-organic medium, when the cyanuro halide is dissolved in an organic solvent such as acetone, benzene, toluene or chlorobenzene, and the aqueous solution added dropwise to the amino compound. By the addition of a dispersion agent the reaction is completed more quickly and purer products are obtained.

The substitution of the first halogen atom of the cyanuro halide takes place, for example, at temperatures ranging from 0° to 5°C and at a pH ranging from 1 to 7. The condensation of the second halogen atom is conveniently effected at temperatures ranging from 20° to 40°C and at weakly acid to weakly alkaline reaction, e.g. at a pH ranging from 4 to 8. The third halogen atom is preferably reacted at temperatures ranging from 40° to 100°C and at a pH from 4 to 10.

The hydrochloric acid freed in the course of the reaction is conveniently neutralised with alkali, e.g. alkali metal hydroxides, bicarbonates, or carbonates, or tertiary organic amines, e.g. tri-(2-hydroxyethyl)-amine.

The reactions of the cyanuro halide with the corresponding amines of formulae IV, V and VI may be effected in any desired order. Preferably, the cyanuro halide is first reacted with the amine of formula IV, then with the diamine of formula V and finally with the amine of formula VI.

For the introduction of the radical $R_6$, the treatment with alkylation agents is effected in accordance with conventional quaternations [see Houben-Weyl *Methoden der Organischen Chemie* Vol. XI/2 (4th edition, 1958) pages 591–613] and preferably carried out at temperatures ranging from 0° to 150°C, conveniently from approximately 15° to 110°C, in an inert solvent, e.g. a low molecular alkane carboxylic acid or particularly a low molecular alcohol such as methanol, optionally in the presence of water or in an excess of alkylation agent.

The resulting compounds of formula I may be isolated and purified in conventional manner, e.g. by salting out, precipitating by the addition of acids, or evaporating the reaction solution, whereby products in powder form are obtained. After separating the salts there may also be obtained liquid preparations by the addition of a solvent aid, e.g. glycol, glycolic ether, formamide, acetamide, of urea or a mono-, di- or tri-(2-hydroxyethyl)- or -(2-hydroxypropyl)-amine.

As will be appreciated, the particular significance of M may be introduced during the production of compounds of formula I by employing compounds of formula IV and V in which M has such significance. Alternatively, however, and again as will be appreciated, the significance of M, as obtained initially in the compounds of formula I may be exchanged, in conventional manner, for any other desired significance thereof.

Similarly, for the anion $A^-$, where such is present in the compounds of formula I, the particular significance thereof may be introduced during the process for producing the compounds of formula I, e.g. by use of appropriate alkylating agents for the introduction of $R_6$. Alternatively, however, and as will be appreciated, exchange of one significance of $A^-$ for another may be effected in known manner in compounds of formula I, e.g. as disclosed in [Houben-Weyl, *Methoden der Organischen Chemie* Vol. XI/2 (4th edition 1958) pages 620 et seq.]. Thus the particular compound may be dissolved in water or an aqueous-organic medium and reacted with a silver salt e.g. silver nitrite or acetate, when a halogen anion ($Cl^-$, $Br^-$, $I^-$) has to be substituted by another anion e.g. nitrate or acetate ion, or with a barium salt, when a sulphate anion has to be substituted by another anion. This exchange may be effected in one or more steps, e.g. through the carbonate or hydroxide, or with the aid of ion exchangers.

The compounds of formula I are useful as optical brightening agents. Particularly, the compounds of formula I are useful as optical brightening agents for substrates comprising cellulose. Such substrates may, for example, be in loose fibre, thread, yarn, knitted, woven, non-woven, paper, felt, velvet, carpet or homogeneous mass (viscose) form.

The application of compounds of formula I is preferably carried out in connection with a finishing or high-grade finishing of the substrates.

Particular applications of the compounds of formula I are as follows:

a. the brightening of cellulosic textiles, particularly cotton, from a long bath,
b. the brightening of cellulosic textiles, particularly cotton, according to a padding process (especially continuous padding process),
c. the brightening and simultaneous finishing of cellulosic textiles, particularly cotton, in a synthetic resin bath,
d. the optical brightening of viscose rayon by employing the compounds of formula (I) in the spinning mass during the production process,
e. the optical brightening of papers in the stock, or surface treatment of the formed papers, (c) and (e) being particularly preferred applications.

The compounds of formula (I), particularly the alkali metal salts thereof, are well soluble in water. Comparatively highly concentrated liquid preparations (e.g. 10 to 30%) may be produced therewith.

When using the compounds from a long bath, 0.05 to 0.8 % of the optical brightener, in relation to the substrate, are preferably used. The bath length is preferably in a ratio of 1:10 to 1:50 and the treatment temperature preferably in the range of 30° to 60°C. The bath may contain other additives.

The compounds of formula I are suitable as brightening agents for padding processes, particularly continuous padding processes, where the brightening concentration in the treatment bath may be kept almost constant. The concentration of the optical brightener is preferably from 0.02 to 1.2 %, conveniently from 0.05 to 0.8 %, in relation to the substrate. The brightener may be fixed in accordance with the cold retention process or in the heat, optionally after an intermediate drying.

In the finishing of textiles (fabrics or nonwoven fabrics) with binding agents, especially synthetic resins, the optical brightener may be added to the synthetic resin either in the treatment bath or before. 0.02 to 1.2%, preferably, 0.05 to 0.8% of the optical brightener, in relation to the substrate, are added. The fixation of the brightener and the cross-linking of the finishing agent may be effected in accordance with the method of wetting out in the cold or by heat treatment, optionally after an intermediate drying. The obtained brightenings are brilliant and of intense fluorescence.

Due to their stability in a strongly acid bath and towards salts such as magnesium chloride and zinc chloride, the compounds of formula I are eminently suitable for the optical brightening and a simultaneous crease-proof finish of cotton.

Further, the compounds of formula I are suitable for the brightening of paper. For the brightening of paper in the stock, they are preferably used in the range of 0.01 to 0.5 %, based on the weight of the cellulose.

The compounds of formula I are also suitable for the brightening of paper after sheet formation. This may be effected by adding the optical brightener to the coating pastes, sizing solutions or suspensions (sizing press) or merely by applying to the paper dilute solutions.

Any kind of fine and coarse paper of bleachable or unbleachable cellulose may be used.

For the treatment of paper in the sizing press, sizing liquors are suitable which contain, per liter of the treatment liquor, 0.3 to 8, preferably 0.5 to 6 g of the compound of formula I. The amount of the brightener will naturally depend on the amount and kind of the binding agent used, the paper and on the degree of whiteness required. The concentration of the binding agent is usually from 2 to 15 % of the bath. For the surface treatment of papers, other additives may also be added to the treatment bath, e.g. white pigments or fillers. They are usually added in amounts of approximately 10 to 65 %, based on the coating paste. The binding agents are used in amounts of approximately 5 to 25 %. The optical brightener is preferably used in amounts of approximately 0.3 to 6 g per liter of coating paste.

By the addition of polyvinyl chloride and/or polyethylene glycol as blending agent for liquid preparations or powder formulations of the optical brighteners, their white effect may considerably be increased. Appropriate binding agents are, for example, decomposed starch, alginates, gelatine, polyvinyl alcohol, polyvinyl pyrrolidone, carboxymethyl cellulose, casein, protein, polyvinylidene chloride or mixtures of these binding agents, the decomposed starch, the polyvinyl alcohol and the carboxy methyl cellulose being preferred. Also suitable are aqueous synthetic resin dispersions based on co-polymerization of acrylic or butadiene styrene resins, the content of synthetic resin being approximately 50 %.

Appropriate fillers and white pigments are the common products such as China-Clay, calcium carbonate, "satic white", "Blancfix", titanium oxide, talc, precipitated aluminium silicates etc. as well as the mixtures thereof.

The coating pastes may additionally contain hyrosoluble poly- or metaphosphates and, as wetting agents, unsulphated or sulphated higher alkanol or alkylphenol polyglycolic ethers of 8 – 14 alkyl carbon atoms and 1 to 20 ethylene oxide groups. In order to obtain good flow properties, an alkali coating paste is preferably used. The alkaline reaction is conveniently effected with ammonium hydroxide or with sodium or potassium hydroxides, -carbonates, -borates, -perborates or mixtures thereof.

The compounds of formula I show acid and salt resistance; they are particularly resistant towards the action of aluminium ions and are well compatible with binding agents and fillers used for the surface finishing of papers.

The resulting optical brightenings show a neutral to weakly greenish white shade.

In the following Examples the parts, unless otherwise stated, are by weight and the percentages likewise. The temperatures are in degrees centigrade. The parts by weight relate to the parts by volume as grams to milliliters.

EXAMPLE 1

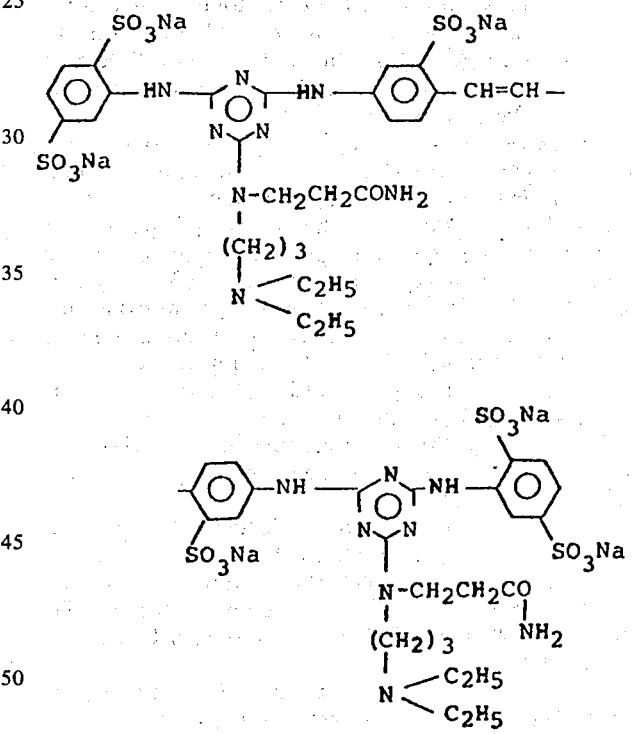

100 Parts of cyanuro chloride are dissolved in 378 parts of acetone and the solution is entered into 2580 parts of ice water with stirring. A solution of 161 parts of 1-aminobenzene-2,5-disulphonic acid (sodium salt) in 900 parts of water is run into the resulting cyanuro chloride suspension, at 0° to 5°, over the course of 60 minutes. The freed acid is neutralized with a 15% sodium carbonate solution and thus the pH of the mixture is kept at 2–3.

The pH is subsequently adjusted to 6 at a temperature of 0° to 5° by means of a sodium carbonate solution. the mixture is stirred at this pH at 5°–10° over the course of 2 to 3 hours, whereby the aminobenzene disulphonic acid is virtually reacted. A solution of 106.8 parts of 4,4'-diaminostilbene-2,2'-disulphonic acid sodium in 775 parts of water is then added to the clear reaction solution, the pH is kept at 6.5 to 7 by the addition of sodium carbonate and the mixture is stirred at 20°–30° over the course of 3 to 4 hours. After this period no diazotizable amine is detected in the clear reaction solution. To the solution of the resulting hexasodium salt of the 4,4'-bis-[2''-chloro-4''-(2,5-disulphenylamino)-s-triazinyl-(6'')-amino]-stilbene-2,2'-disulphonic acid are subsequently added 115 parts of β-(γ-diethylaminopropylamino)-propionic acid amide (addition product consisting of acrylic amide and 3-diethylamino-1-propylamine), the pH raising for a short time to approximately 10. The mixture is heated to 95°–100° with the distillation of acetone. 23.8 Parts of a 15 % sodium carbonate solution is added dropwise thus, that the pH is in the range of 8 to 9. After the addition of sodium carbonate solution the mixture is boiled at slight reflux for 1 to 2 hours. The mixture is subsequently treated at approximately 85° with 5 parts of stripping coal, filtered and evaporated under vacuum. The resulting optical brightener of the formula above given forms an almost colourless powder which may be readily dissolved in water. The 1% aqueous solution shows intense blue fluorescence which is even intesified by acidification with 20% hydrochloric acid. Even at a pH value of below 1 the 1 % solution shows no turbidity. The product may be used for the optical brightening of cellulosic substrates such as paper, cotton and substrates of regenerated cellulose.

The brightenings show a maximum white and a neutral white shade.

The above-mentioned β-(γ-diethylaminopropylamino)-propionic acid amide is obtained by stirring, at 40°, 71 parts of acrylic acid amide into 130 parts of 3-diethylamino-1-propylamine and by continuous stirring for 1 hour at the same temperature.

Products with similar action are obtained by replacing the above-mentioned addition product of the above Example by the addition products indicated in the following Table, the end products being isolated by evaporation under vacuum. All products form weakly coloured powders which are readily soluble in water.

| Expl. No. | Amine | Acrylic acid Derivative | Addition Product |
|---|---|---|---|
| 2 | $C_2H_5$–N(–$C_2H_5$)–$(CH_2)_3$–$NH_2$ | $CH_2$=CH–CN | $C_2H_5$–N(–$C_2H_5$)–$(CH_2)_3$–NH–$CH_2$–$CH_2$–CN |
| 3 | (HO–$CH_2$–$CH_2$)$_2$N–$(CH_2)_3$$NH_2$ | $CH_2$=CH–CO–$NH_2$ | (HO–$CH_2$–$CH_2$)$_2$N–$(CH_2)_3$–NH–$CH_2$–$CH_2$–CO–$NH_2$ |
| 4 | $(C_2H_5)_2$N–$CH_2$–$CH_2$–$NH_2$ | $CH_2$=CH–CO–$NH_2$ | $(C_2H_5)_2$N–$CH_2CH_2$–NH–$CH_2$–$CH_2$–CO–$NH_2$ |
| 5 | O(CH$_2$CH$_2$)$_2$N–$(CH_2)_3$–$NH_2$ | $CH_2$=CH–CO–$NH_2$ | O(CH$_2$CH$_2$)$_2$N–$(CH_2)_3$–NH–$CH_2$–$CH_2$–CO–$NH_2$ |
| 6 | O(CH$_2$CH$_2$)$_2$N–$(CH_2)_3$–$NH_2$ | $CH_2$=CH–CN | O(CH$_2$CH$_2$)$_2$N–$(CH_2)_3$–NH–$CH_2$–$CH_2$–CN |
| 7 | $CH_3CH_2$–N($CH_3CH_2CH_2CH_2$)–$(CH_2)_3$–$NH_2$ | $CH_2$=CH–CO–$NH_2$ | $CH_3CH_2$–N($CH_3CH_2CH_2CH_2$)–$(CH_2)_3$–NH–$CH_2$–$CH_2$–$NHCOCH_2$ |
| 8 | (CH$_2$–CH$_2$)$_2$N–$(CH_2)_3$–$NH_2$ | $CH_2$=CHCONH$_2$ | (CH$_2$–CH$_2$)$_2$N–$(CH_2)_3$–NH–$CH_2$–$CH_2$–$NHCOCH_2$ |
| 9 | (CH$_2$–CH$_2$)$_2$N–$(CH_2)_3$–$NH_2$ | $CH_2$=CH–CN | (CH$_2$–CH$_2$)$_2$N–$(CH_2)_3$–NH–$CH_2$–$CH_2$–CN |
| 10 | CH$_2$(CH$_2$–CH$_2$)$_2$N–$(CH_2)_3$–$NH_2$ | $CH_2$=CHCONH$_2$ | CH$_2$(CH$_2$–CH$_2$)$_2$N–$(CH_2)_3$–NH–$CH_2$–$CH_2$–$NHCOCH_2$ |
| 11 | $CH_3$–N(CH$_2$–CH$_2$)$_2$N–$(CH_2)_3$–$NH_2$ | $CH_2$=CH–CONH$_2$ | $CH_3$–N(CH$_2$–CH$_2$)$_2$N–$(CH_2)_3$–NH–$CH_2$–$CH_2$–$NHCOCH_2$ |
| 12 | $CH_3$–N(CH$_2$–CH$_2$)$_2$N–$(CH_2)_3$–$NH_2$ | $CH_2$=CH–CN | $CH_3$–N(CH$_2$–CH$_2$)$_2$N–$(CH_2)_3$–NH–$CH_2$–$CH_2$–CN |

The alkali salts of the stilbene compounds of Examples 1 to 12 may be converted into the free hexasulphonic acids by treatment with strong mineral acids, the protonizable amino groups being protonized at the same time.

When, for example, a 15 to 20 % solution of the optical brightening agent of Example 1, is adjusted to a pH of about 1 with the addition of approximately 30 % hydrochloric acid, a fine whitish suspension is obtained. When the suspension is filtered off and dissolved, for example by treatment with ammonia or an alkanol amine, comparatively concentrated and stable solutions of the corresponding salts are obtained, which is of advantage in the paper industry.

EXAMPLE 13

15.6 Parts of the compound of Example 1 are dissolved in a mixture of 110 parts of water and 30 parts by volume of isopropyl alcohol. The solution is heated to 50°–60°, the pH adjusted to 9 with the addition of a small quantity of 30 % sodium hydroxide solution and 2.8 parts of dimethyl sulphate, dissolved in 10 parts by volume of isopropyl alcohol, are added. The pH is kept at 8–9 by the addition of 12 % sodium hydroxide solution. After about 15 minutes the reaction is nearly complete. The mixture is stirred at 50°–60° over the course of 30 minutes and is allowed to cool. The course of reaction may be easily observed in a thin layer chromatogramme. A brightening agent of formula

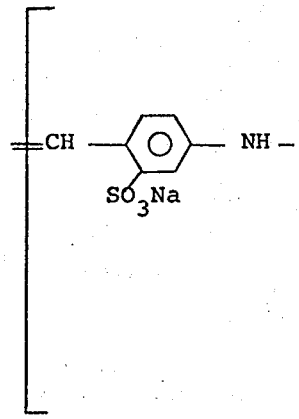

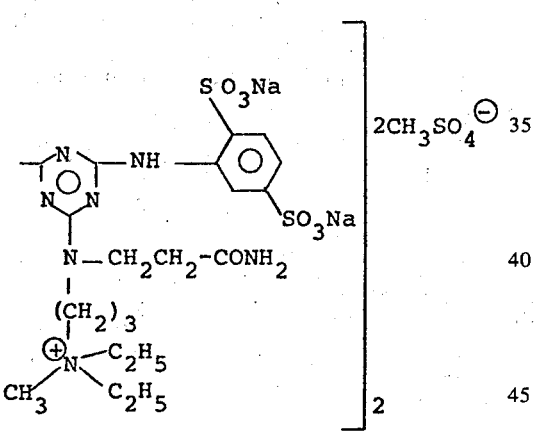

is obtained. This brightening agent is of more polar character than the non-quaternized compound of Example 1.

APPLICATION EXAMPLE A

60 Parts of decomposed starch are stirred in the cold into 600 parts of water and subsequently colloidally dissolved at 80°–90°. To this solution are added 3 parts of sodium polyphosphate, 120 parts of a 50 % synthetic resin dispersion based on a butadiene-styrene-copolymer (e.g. Dow Latex 636 of the firm Dow Chemical Corp. USA), a solution of 4 parts of the compound of Example 1 in 400 parts of water and finally 600 parts of a white pigment (aluminium-magnesium silicate). The mixture is stirred until a homogeneous suspension is obtained.

A sized raw paper, consisting of 50 % of bleached sulphite cellulose and 50 % of mechanical wood pulp and having a surface pH value of 4, is coated in a coating apparatus with the above-described coating paste. An intensely white paper with fastness to printing is obtained.

A higher dose of the whitening agent does not cause an undesired coloration but increases the white effect even more.

By adding to the above described coating paste 4 parts of polyvinyl alcohol as diluting agent, the brightening effect is considerably increased.

By processing as in the above Example but replacing the 4 parts of the compound of Example 1 by a corresponding amount of the compound of Example 13, a similar brightening effect is obtained.

APPLICATION EXAMPLE B

A synthetic resin coating paste is prepared as follows:
A solution of 5 parts of the compound of Example 1, 2 parts of nonylphenol-pentadecaglycol ether and 5 parts of polyethylene glycol (md.wt. 5000–6000) in 300 parts of water is added to 140 parts by volume of a 50 % aqueous synthetic resin dispersion based on a cross-linkable methyl acrylate/methyl methacrylate/styrene copolymer (e.g. ACRONAL S 320 D [BASF]). The mixture is diluted with water to 1000 parts by volume and well stirred.

A sized and filled raw paper of sulphite cellulose is coated with this treatment bath and subsequently dried. A brilliant white paper with fastness to printing is obtained.

APPLICATION EXAMPLE C

50 Parts of decomposed starch are colloidally dissolved over the course of 15 minutes in 900 parts of water at 90°. A solution of 4 parts of the compound of Example 1 in 100 parts of water is added. A sized printing paper is treated with this solution in a sizing press and the paper thus treated is dried at 50°–120°. The paper is of considerably whiter appearance than unbrightened paper.

With sized cardboard the same good results are obtained.

Replacing in the above described solution the brightening agent of Example 1 by the brightening agent of Examples 2 to 13, similarly good results are obtained.

APPLICATION EXAMPLE D

A bleached cotton poplin fabric pre-purified by conventional methods is impregnated at 20° on a padder with an aqueous chemical finishing bath, containing, per liter, 3 g of the compound of Example 1. The impregnated goods are expressed to a liquor absorption of 70 %, based on the dry weight of the fabric, and then directly dried on a pig stenter at a temperature ranging from 140° to 150°, over the course of 10 to 20 seconds.

The cotton poplin fabric, brightened in accordance with this process, shows a high, brilliant brightening effect with a neutral shade. The brightening effect is fast to acids.

By processing in the same way but using in place of the compound of Example 1, the same amount of one of the brightening agents described in Examples 2 to 12, similarly good brightening effects are obtained which show slightly more greenish shades.

APPLICATION EXAMPLE E

A bleached cotton fabric, pre-purified by conventional methods, is impregnated on a padder with a chemical finishing bath at 20°, containing, per liter, the following constituents: 70 g of dimethylolpropylene urea, 3 g of the brightening agent of Example 1 and 20 g of magnesium chloride hexahydrate.

The impregnated goods are expressed to a liquor absorption of 80 %, based on the dry weight of the fabric, dried at 120° and subsequently condensed on a condensation machine at a temperature of 150° over the course of 4 minutes. The fabric obtained in accordance with this process shows wash fastness, a crease-resistant finish and an extremely high neutral degree of whiteness.

By processing in the same way but replacing the aforementioned magnesium salt by 20 parts of zinc chloride or 14 parts of zinc nitrite, similarly good results are obtained.

Using in place of the compound of Example 1 a corresponding amount of the compounds of Examples 2 to 13, similarly good brightening effects are obtained.

What is claimed is:

1. A compound of formula I,

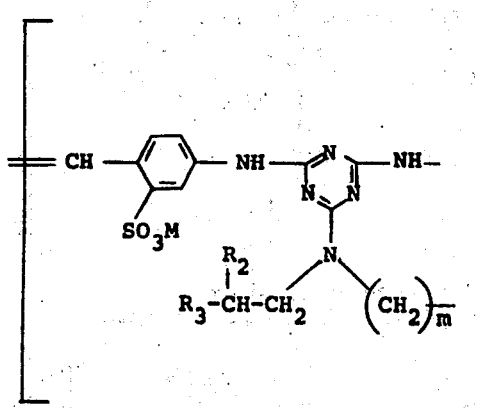

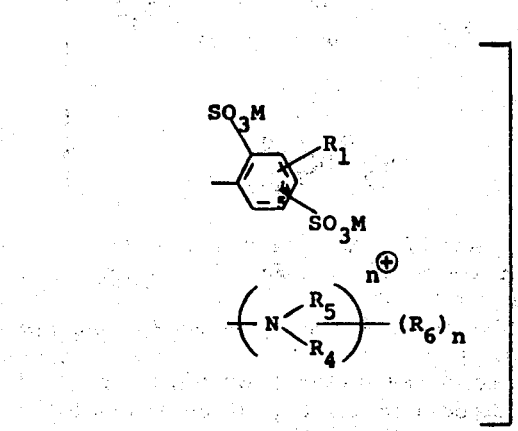

wherein
  $R_1$ is hydrogen, chlorine or $C_{1-4}$ alkyl,
  $R_2$ is hydrogen or methyl,
  $R_3$ is cyano or —$CONR_7R_8$, in which either $R_7$ and $R_8$, independently, each is hydrogen, $C_{1-4}$ alkyl or $C_{2-4}$ hydroxyalkyl, or $R_7$ and $R_8$, together with the nitrogen atom to which they are attached, are a pyrrolidine, piperidine or morpholine radical,
  either $R_4$ and $R_5$, independently, each is $C_{2-4}$ alkyl or $C_{2-4}$ hydroxyalkyl,
  or $R_4$ and $R_5$, together with the nitrogen atom, form a radical of formula (a),

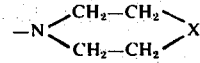

in which —X— is —$CH_2$—, —O—, —S—, a direct bond, or —$NR_9$—, in which $R_9$ is $C_{1-3}$ alkyl or $C_{2-3}$ hydroxyalkyl,
  $R_6$ is hydrogen, $C_{1-6}$ alkyl or $C_{2-4}$ alkyl substituted by hydroxy, cyano or carbamoyl,
  M is hydrogen or a non-chromophoric cation,
  $A^-$ is a non-chromophoric anion,
  $m$ is 2 or 3, and
  $n$ is 0 or 1,
the —$SO_3M$ group, shown floating, being bound to the 4- or 5-position of the benzene ring and, when $n$ is 1, $R_6$ being bound either to the nitrogen or, when $NR_4R_5$ is a thiomorpholino ring, to the nitrogen or to the sulfur thereof or, when $NR_4R_5$ is a piperazine ring, to one or the other of the nitrogens thereof.

2. A compound of claim 1, wherein $R_1$ is hydrogen.
3. A compound of claim 1, wherein $R_2$ is hydrogen.
4. A compound of claim 2, wherein $R_2$ is hydrogen.
5. A compound of claim 4, wherein $R_3$ is —CN or —$CONH_2$.
6. A compound of claim 5, wherein either $R_4$ and $R_5$, independently, each is $C_{2-4}$ alkyl or hydroxyalkyl or $R_4$ and $R_5$ are a radical (a), in which —X— is —$CH_2$, —O—, a direct bond or —$NR_9$—.
7. A compound of claim 6, wherein any $R_9$ is methyl.
8. A compound of claim 6, wherein $R_6$ is hydrogen, methyl or ethyl.
9. A compound of claim 8, of formula I',

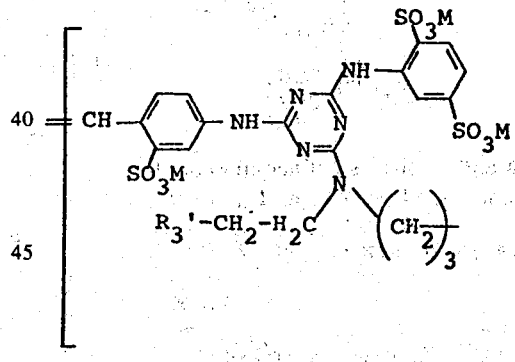

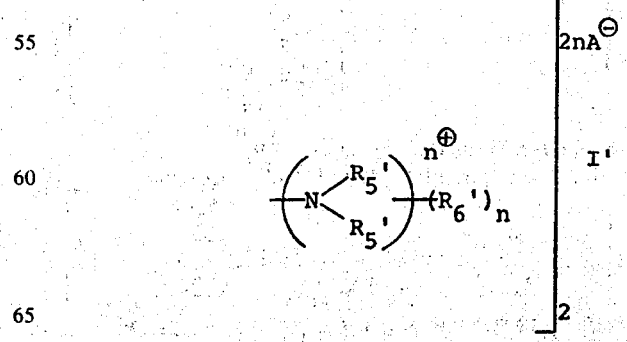

in which $R_3'$ is —CN or —$CONH_2$,
either $R_4'$ and $R_5'$, independently, each is $C_{2-4}$ alkyl, or $R_4'$ and $R_5'$, together with the nitrogen atom, are a pyrrolidine, piperidine, morpholine or N-methylpiperazine ring, $R_6'$ is hydrogen, methyl or ethyl, n is 2 or 3, M is a hydrogen atom or a non-chromophoric cation, and $A^-$ is a non-chromophoric anion.

10. A compound of claim 9 and of formula

[structural formula]

in which M is as defined in claim 9.

11. A compound of claim 9 and of formula

[structural formula]

in which M and $A^-$ are as defined in claim 9.

12. A compound of claim 11, wherein $A^-$ is $CH_3SO_4^-$.

13. A compound of claim 9 and of formula

[structural formula]

in which M is as defined in claim 9.

14. A compound of claim 9 and of formula

[structural formula]

in which M is as defined in claim 9.

15. A compound of claim 9 and of formula

[structural formula]

in which M is as defined in claim 9.

16. A compound of claim 9 and of formula

[structural formula]

in which M is as defined in claim 9.

17. A compound of claim 9 and of formula

[structural formula]

in which M and $A^-$ are as defined in claim 14.

18. A compound of claim 17, wherein $A^-$ is $CH_3SO_4^-$.

19. A compound of claim 1, wherein $R_3$ is —CN or —$CONH_2$.

20. A compound of claim 1, wherein either $R_4$ and $R_5$, independently, each is $C_{2-4}$ alkyl or hydroxyalkyl or $R_4$ and $R_5$ are a radical (a), in which —X— is —$CH_2$—, —O—, a direct bond or —$NR_9$—.

21. A compound of claim 20, wherein any $R_9$ is methyl.

22. A compound of claim 1, wherein $R_6$ is hydrogen, methyl or ethyl.

23. A process for optically brightening a cellulosic substrate comprising applying thereto or incorporating therein a compound of claim 1.

24. A process according to claim 23, wherein said substrate comprises cotton.

25. A process according to claim 23, wherein said substrate is paper, the compound being either incorporated into the stock or applied after sheet formation.

26. A process according to claim 23, wherein said substrate comprises resin finished cotton.

* * * * *